(12) United States Patent
Kuypers et al.

(10) Patent No.: US 10,247,656 B2
(45) Date of Patent: Apr. 2, 2019

(54) SINGLE-CELL MICROCHAMBER ARRAY

(75) Inventors: Franciscus Albertus Kuypers, El Cerritos, CA (US); Won Chul Lee, Berkeley, CA (US); Albert P. Pisano, Walnut Creek, CA (US)

(73) Assignee: CHILDREN'S HOSPITAL & RESEARCH CENTER AT OAKLAND, Oakland, CA (US)

( * ) Notice: Subject to any disclaimer, the term of this patent is extended or adjusted under 35 U.S.C. 154(b) by 619 days.

(21) Appl. No.: 13/224,064

(22) Filed: Sep. 1, 2011

(65) Prior Publication Data

US 2012/0065082 A1     Mar. 15, 2012

Related U.S. Application Data

(60) Provisional application No. 61/381,408, filed on Sep. 9, 2010.

(51) Int. Cl.
| | | |
|---|---|---|
| *C40B 30/00* | (2006.01) | |
| *G01N 15/14* | (2006.01) | |
| *G01N 15/10* | (2006.01) | |
| *G01N 15/00* | (2006.01) | |

(52) U.S. Cl.
CPC ..... *G01N 15/1484* (2013.01); *G01N 15/1056* (2013.01); *G01N 15/1475* (2013.01); *G01N 2015/0069* (2013.01); *G01N 2015/1486* (2013.01)

(58) Field of Classification Search
USPC .......................................................... 506/7
See application file for complete search history.

(56) References Cited

U.S. PATENT DOCUMENTS

| | | | | |
|---|---|---|---|---|
| 2004/0058423 A1* | 3/2004 | Albritton et al. | ........ | 435/173.7 |
| 2005/0014201 A1* | 1/2005 | Deuthsch | ........ | 435/7.2 |
| 2006/0216203 A1* | 9/2006 | Fuller | ........ | B01L 3/5085 422/82.01 |
| 2007/0243523 A1* | 10/2007 | Ionescu-Zanetti et al. | ........ | 435/4 |
| 2009/0117555 A1* | 5/2009 | Kuypers | ........ | G01N 15/147 435/6.14 |
| 2010/0022416 A1* | 1/2010 | Flemming | ........ | B01L 3/5085 506/39 |

OTHER PUBLICATIONS

Deutsch, M. et al 1994 Cytometry 16: 214-226.*
Sasuga et al 2008 Analytical Chemistry 80: 9141-9149.*
Jackman et al. (Analytical Chemistry, 1998, 70, pp. 2280-2287).*
Brown et al. J.R. Soc. Interface, 2008, 5, S131-S138.*

* cited by examiner

*Primary Examiner* — Karla A Dines
(74) *Attorney, Agent, or Firm* — David R. Stevens; Stevens Law Group

(57) ABSTRACT

An apparatus for analyzing individual cell composition in a heterogeneous cell population may include, in one embodiment, a deposition plate having an array of microwells disposed therein, and a cover plate substantially overlying the deposition plate. A pair of electrodes may be associated with one or more of the microwells, and may be configured to generate an electric field within the associated microwell.

23 Claims, 10 Drawing Sheets

SINGLE-CELL MICROCHAMBER ARRAY

RELATED APPLICATIONS

This application claims priority based on U.S. Provisional Application No. 61/381,408, filed on Sep. 9, 2010.

This invention was made with government support under contract number 5R21HL092535 awarded by the National Institutes of Health (NIH). The government has certain rights in the invention.

BACKGROUND

This invention relates to apparatus and methods for analyzing cytoplasmic components of single cells in large heterogeneous cell populations.

Cell cytoplasm contains a complex mixture of chemicals and enzymes that are important for biochemical pathways and essential for the life of a cell. Abnormalities in the cytoplasm of subpopulations of cells are often a hallmark of pathology. While measurement of cytoplasmic components is essential to study cell physiology, most analysis methods only provide information regarding the cell population as a whole, not for individual cells or subpopulations of cells.

For example, only the overall concentration, but not the distribution of ATP concentrations in a heterogeneous cell population can be assessed using classical ATP measurements. ATP levels in cells can be sensitively measured using commercially available chemiluminescence assays. However, such analysis will only provide information of the cell population as a whole. In other words, a drop of ten percent (10%) in overall ATP concentration could be interpreted as ninety percent (90%) ATP remaining in all cells, or alternatively, that ten percent (10%) of the cells have no ATP at all. The consequences of a subpopulation of cells that is unable to maintain ATP seem obvious, but the determination of such a subpopulation is more difficult. Similar examples hold for many cytoplasmic components.

Single-cell analysis is thus an important tool in biology, as it defines properties of individual cells in heterogeneous cell populations. Current techniques, including flow cytometry, laser-scanning cytometry, and automated microscopy, are mainly used to define cell surface markers. Few probes are available that penetrate the plasma membrane and allow measurement of cytoplasmic components in single cells. Further, most cell analysis methods based on single-cell lysis are impractical to measure a significant number of cells in a reasonable amount of time to establish statistically relevant distributions in a cell population. The measurement of enzyme activity in single cells adds another complexity, as it requires monitoring of substrate use over time and under well-defined conditions.

In view of the foregoing, what are needed are apparatus and methods to analyze the stochastic distribution of cytoplasmic components in a heterogeneous cell population. Beneficially, such apparatus and methods would promote low cost, easy fabrication, high throughput, rapid measurement, and accurate correlation of cytoplasmic components with cell surface markers in a complex cell population. Such apparatus and methods are disclosed and claimed herein.

BRIEF DESCRIPTION OF THE DRAWINGS

In order that the advantages of the invention will be readily understood, a more particular description of the invention briefly described above will be rendered by reference to specific examples illustrated in the appended drawings. Understanding that these drawings depict only typical examples of the invention and are not therefore to be considered limiting of its scope, the invention will be described and explained with additional specificity and detail through the use of the accompanying drawings, in which:

FIG. 2b is a microscopic image top view of cells contained within the microwells illustrated in FIG. 2a;

FIG. 3b is a microscopic image top view of cells contained with the closed microchambers of FIG. 3a;

FIG. 4b is a microscopic image top view of the lysed cells of FIG. 4a;

FIG. 5b is a fluorescence image and associated graph of the various possibilities associated with cell containment and lysing illustrated in FIG. 5a;

DETAILED DESCRIPTION

The invention has been developed in response to the present state of the art, and in particular, in response to the problems and needs in the art that have not yet been fully solved by currently available cytoplasmic analysis methods and apparatus. Accordingly, the invention has been developed to provide a novel apparatus and method for analyzing individual cell composition in a heterogeneous cell population. The features and advantages of the invention will become more fully apparent from the following description and appended claims and their equivalents, and also any subsequent claims or amendments presented, or may be learned by practice of the invention as set forth hereinafter.

In one embodiment, an apparatus for analyzing individual cell composition in a heterogeneous cell population may include a deposition plate having an array of microwells disposed therein, and a cover plate substantially overlying the deposition plate. A pair of electrodes may be associated with one or more of the microwells, and may be configured to generate an electric field within the associated microwell.

In another embodiment, a method for analyzing individual cell composition in a heterogeneous cell population may include depositing a cell suspension onto a deposition plate. The deposition plate may include an array of microwells disposed therein. The cell suspension may include a heterogeneous cell population. Covering the deposition plate may isolate a single cell from the heterogeneous cell population in one or more of the microwells. An electrical field may then be generated within one or more of the microwells to lyse the single cell.

It will be readily understood that the components of the present invention, as generally described and illustrated in the Figures herein, could be arranged and designed in a wide variety of different configurations. Thus, the following more detailed description of the embodiments of apparatus and methods in accordance with the present invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

As used herein, the term "cell" refers to any eukaryotic or prokaryotic cell, living or dead. The term "cytoplasm," as used herein, refers broadly to the entire contents of a cell within the cell membrane, and may include the intracellular fluid as well as contents of the cell nucleus and other organelles within the cell.

Figure 1:
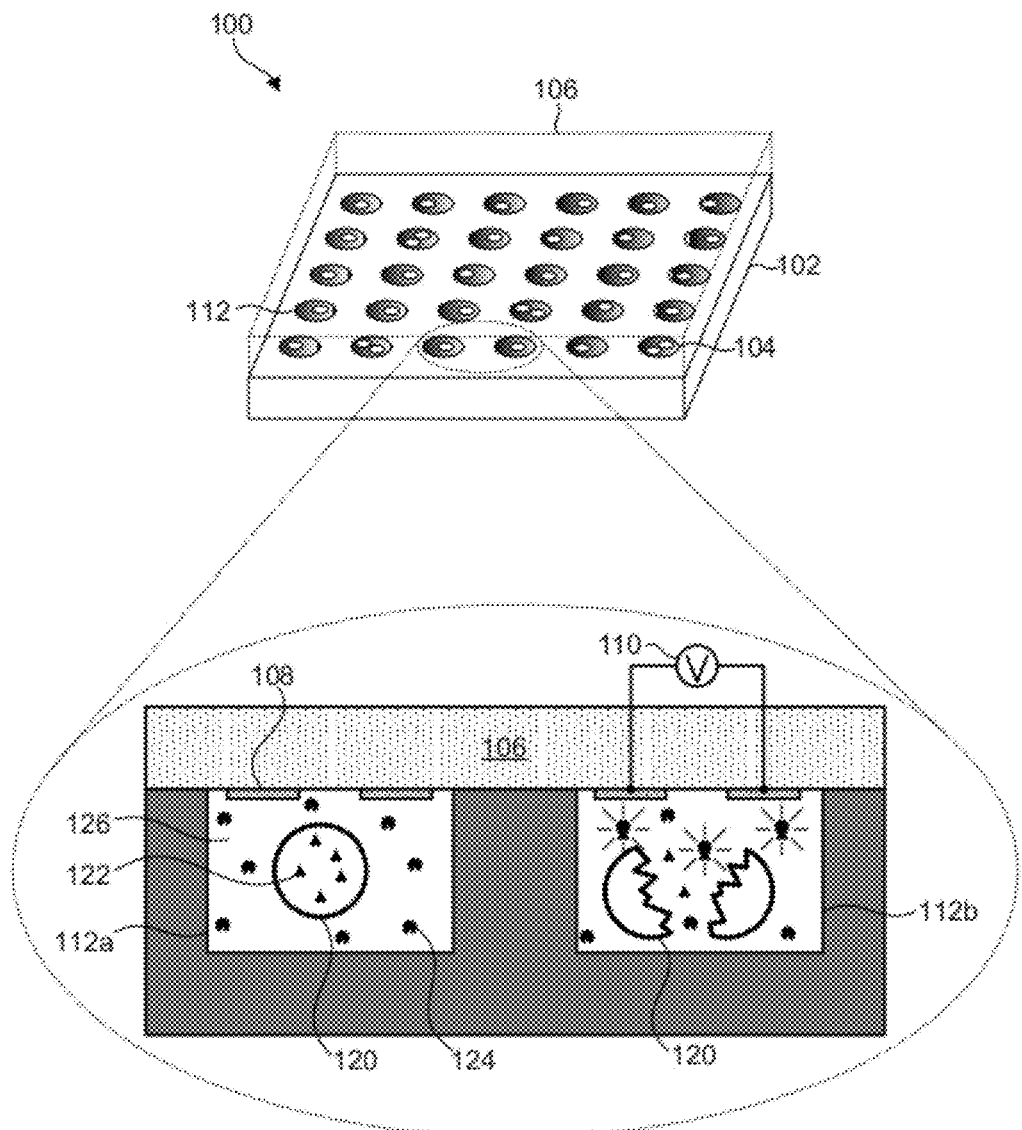
FIG. 1 is a perspective view of an apparatus for analyzing individual cell composition in a heterogeneous cell population in accordance with certain embodiments of the invention.

With reference now to FIG. 1, one embodiment of an apparatus 100 for analyzing cytoplasmic components of single cells in large, heterogeneous cell populations will be described. The apparatus 100 may include an array of open microwells 104 disposed in a deposition plate 102. Individual cells may be collected, isolated and lysed in the microwells 104 to create a reaction mixture of intracellular cytoplasm with extracellular detection agents.

The apparatus 100 may include a cover plate 106 covering the deposition plate 102 to form isolated, closed microchambers 112 corresponding to each open microwell 104. A pair of electrodes 108 may be associated with one or more microchambers 112, and may be configured to generate an electric field within the associated microchamber 112. This applied voltage may effectively lyse a cell therein to facilitate cytoplasmic analysis on a single-cell basis.

The deposition plate 102 and cover plate 106 may be separately fabricated using micro-fabrication techniques and materials that are compatible with cells and cell buffer solutions. In one embodiment, the deposition plate 102 may be fabricated from polydimethylsiloxane ("PDMS"), or any other suitable material known to those in the art. Microwells 104 may be formed therein according to known micromolding or other fabrication techniques. Dimensions and pitches of microwells 104 may vary according to specific cell properties and desired apparatus 100 performance, as discussed in more detail below.

In one embodiment, the deposition plate 102 includes an array of microwells 104 distributed in one hundred rows and one hundred columns, or ten thousand (10,000) microwells 104 of approximately 1,000 fL each. An apparatus 100 in accordance with embodiments of the invention thus enables rapid cytoplasmic analysis of populations of at least ten thousand individual cells in parallel. Slight changes in the design may enable cytoplasmic analysis of populations of one hundred thousand or one million individual cells, or more. Such numbers allow the definition of distribution curves in large cell populations similar to flow cytometry, but focused on cytoplasmic components rather than cell surface markers.

Like the deposition plate 102, the cover plate 106 may also be fabricated from commonly used micro-fabrication materials compatible with cells and cell buffer solutions. Such materials may include, for example, glass, PDMS, or any other suitable material known to those in the art. In any event, at least one of the cover plate 106 and deposition plate 102 may be substantially flexible to promote rapid collection and isolation of single cells in the microchambers 112. Indeed, embodiments of the apparatus 100 may enable collection of cells from an out-of-plane direction without complex microfluidic channels and valves. Further, either or both of the cover plate 106 and the deposition plate 102 may be substantially transparent to facilitate optical measurements and analysis of cytoplasmic components.

Electrodes 108 may be fabricated from, for example, gold or gold alloys, indium tin oxide ("ITO"), or any other suitable, electrically conductive material known to those in the art. In certain embodiments, as discussed in more detail below, a layer of chromium-gold alloy or ITO may be deposited on a glass wafer or other suitable material, and in some embodiments, may be geometrically patterned to produce a cover plate 106 with electrodes 108.

In certain embodiments, the electrodes 108 may be connected to a power source 110 to generate an electric field within at least one microchamber 112. The applied voltage may lyse a cell 120 contained within the microchamber 112 to release the cytoplasm 122 into a surrounding medium or buffer 126.

A method for analyzing individual cell composition in a large, heterogeneous cell population is illustrated in FIGS. 2-5. Each Figure depicts both a cross-sectional rendition and a microscopic image corresponding to a method step. For example, FIG. 2a is a side cross-sectional view illustrating cell-loading in accordance with certain embodiments, while FIG. 2b is a microscopic image top view of the cells 120 of FIG. 2a. The microscopic image top views of FIGS. 2b, 3b, 4b, and 5b depict red blood cells analyzed in accordance with an exemplary embodiment of the invention.

Figure 2A:
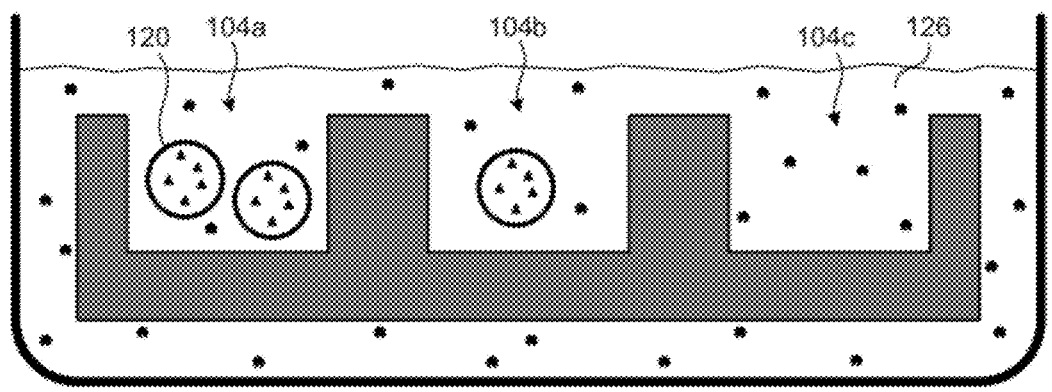
FIG. 2a is a side cross-sectional view of a deposition plate having a cell suspension loaded in microwells in accordance with certain embodiments of the invention.
Figure 2B:
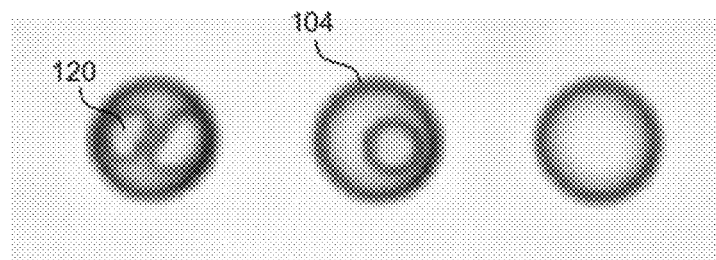

Referring now to FIGS. 2a and 2b, one step of a method for analyzing individual cell composition in accordance with embodiments of the invention may include applying a cell suspension to the array of open microwells 104 disposed in a deposition plate 102. The microwells 104 may be loaded by adding a drop of a cell suspension to the top of the array. The cell suspension may include, for example, red blood cells 120, and a buffer solution 126 including detection agents, such as Ca++. A simple flow of the buffer 126 or other suitable fluid across the top of the array may remove cells 120 not contained in the microwells 104.

As shown in FIG. 2b, one embodiment of an apparatus 100 in accordance with the invention may include microwells 104 having a diameter of approximately 11 μm and a well depth of approximately 10 μm. These microwell 104 dimensions may be specifically selected for the purpose of collecting, isolating, and analyzing red blood cells 120. One skilled in the art will recognize that microwell 104 dimensions may vary depending on dimensions of cells to be collected.

Figure 3A:
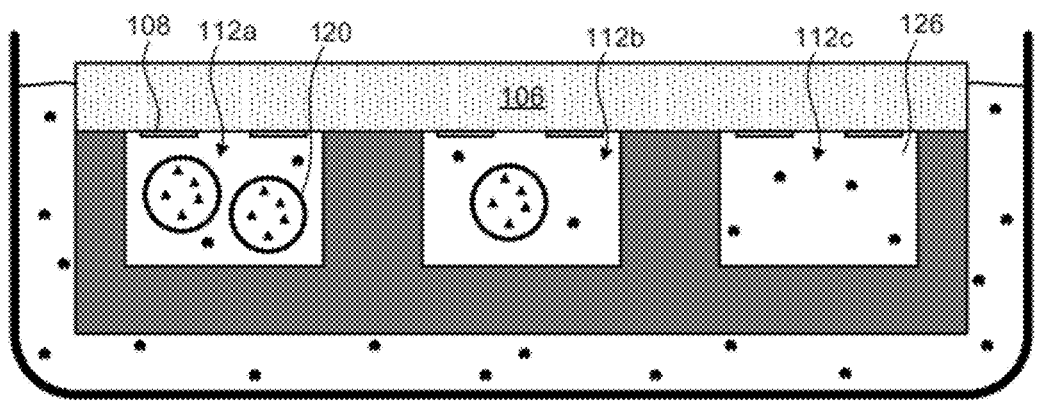
FIG. 3a is a side cross-sectional view of a cover overlying a deposition plate to form closed microchambers in accordance with embodiments of the present invention.

Once loaded, cells 120 may be effectively isolated by covering the array of microwells 104 with a cover plate 106. As shown in FIG. 3a, applying the cover plate 106 in this manner may form closed microchambers 112 corresponding to the previously open microwells 104 of FIG. 2a. In some embodiments, the cover plate 106 may be press-fit to the deposition plate 102, or may be otherwise secured to the deposition plate 102 to effectively seal each microchamber 112 with respect to each other microchamber 112. In this manner, the volume of buffer solution 126 (including detection agents) and cells 120 contained within the microchambers 112 may also be secured. In some embodiments, microelectrodes may be patterned on the cover plate 106 such that a pair of electrodes 108 corresponds to each microchamber 112.

Figure 3B:
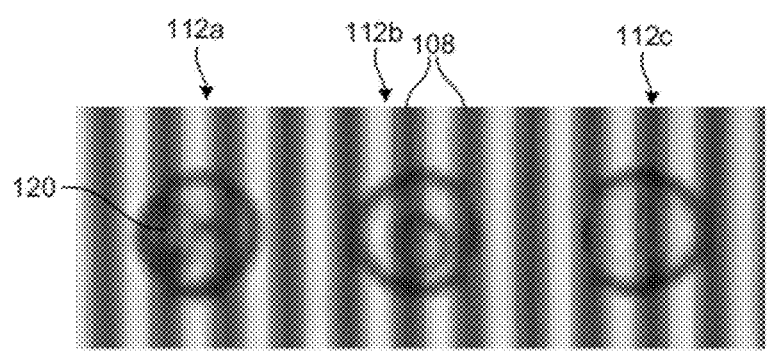

At this point, the microchambers 112 are loaded and may be analyzed for cell count. Indeed, obtaining statistically relevant data may depend on the ability to distinguish microchambers 112 that have no cells, a single cell, or multiple cells. As shown in FIG. 3b, known imaging techniques, such as microscopy, fluorescence, chemiluminescence, absorbance, scanning, or charge-coupled device ("CCD") technology, may be utilized to identify no cell, single cell, and multiple-cell microchambers 112. In this manner, single-cell microchambers 112 demonstrating high reactivity after incubation may be distinguished from multiple-cell microchambers 112 demonstrating increased reactivity simply due to an increased number of cells 120 per microchamber 112.

In certain embodiments, only single-cell microchambers 112b may be statistically relevant. Accordingly, multiple-cell microchambers 112a may be discarded for purposes of further cytoplasmic analysis. Microchambers 112c with no cells may also be discarded, or used for calibration purposes.

Figure 4A:
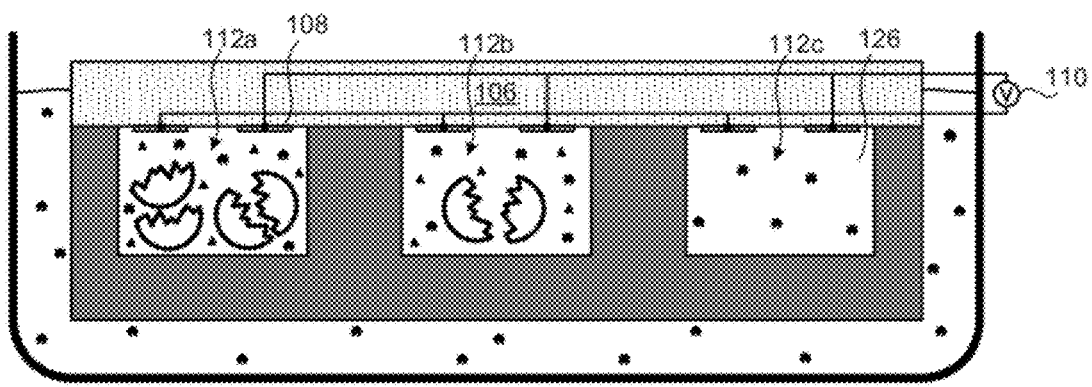
FIG. 4a is a side cross-sectional view of closed microchambers associated with electrodes activated by a power source to lyse cells therein.
Figure 4B:
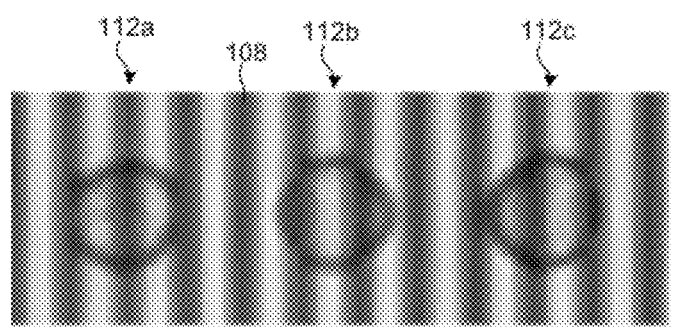

Referring now to FIGS. 4a and 4b, a power source 110 may be actuated to apply a voltage pulse across electrodes 108 associated with each microchamber 112. The voltage pulse may disrupt the plasma membrane of a cell 120 contained within the associated microchamber 112. Of course, one skilled in the art will recognize that the voltage and/or frequency of the pulse may be varied according to the type of cell contained within the microchamber 112, and the desired magnitude of breakdown. For example, voltage and/or frequency may be increased to disrupt the plasma membrane as well as the nuclear membrane or the lipid bilayer of organelles within the cell 120.

Cytoplasm and other cell contents may then be released into the surrounding medium 126. This may create a reaction mixture of cytoplasm and detection agents in the surrounding medium 126. As shown in FIG. 4b, known image analysis techniques may verify breakdown of the cell membrane after application of the voltage pulse to the microchamber 112.

Figure 5A:
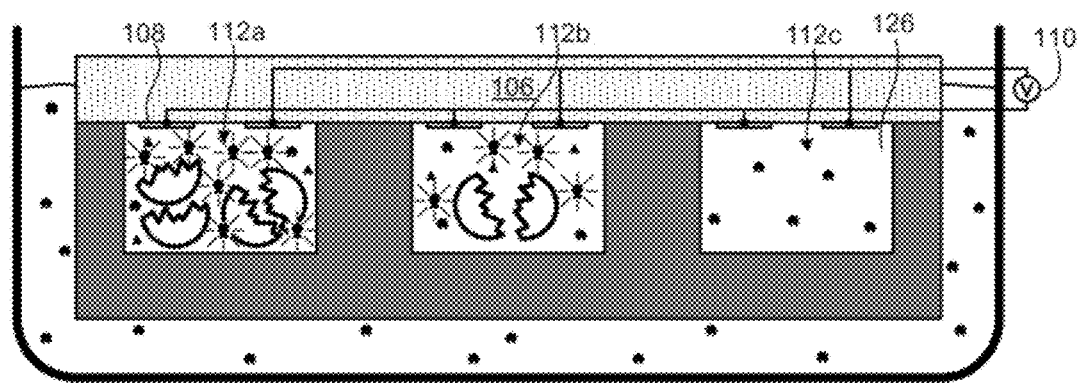
FIG. 5a is a side cross-sectional view of closed microchambers showing various possibilities associated with cell containment and lysing in accordance with embodiments of the invention.
Figure 5B:
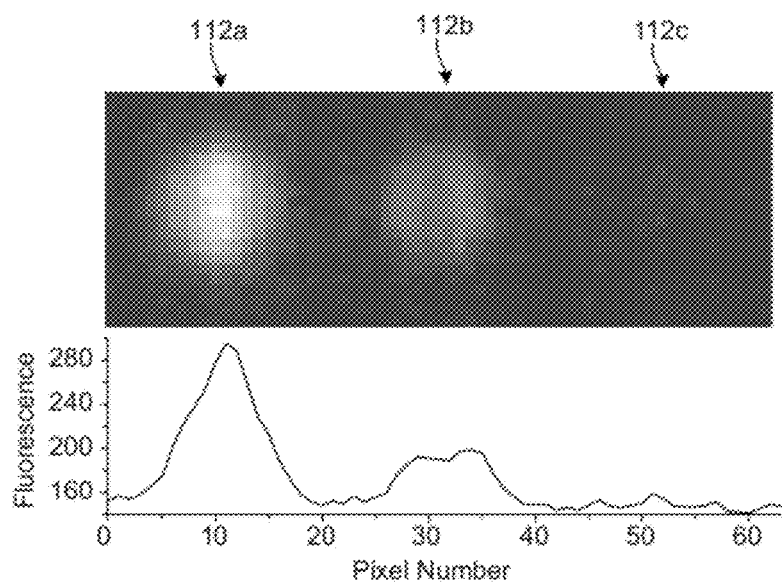

Referring now to FIGS. 5a and 5b, the reaction mixture resulting from release of the cytoplasm into the surrounding medium 126 may be incubated within each microchamber 112 for further cytoplasmic analysis. Each microchamber 112 may be substantially isolated from each other microchamber 112 as discussed above, thus minimizing a risk of dilution or contamination of cell contents over time. As a result, cytoplasmic analysis in accordance with embodiments of the present invention may not be limited to cytoplasmic components associated with fast reaction times.

Indeed, unlike the prior art, certain embodiments may enable measurement and analysis of enzymatic and other chemical reactions associated with varying reaction rates. Reaction mixtures in each microchamber 112 may be incubated for a desired period of time to allow for various enzymatic and other reactions prior to optical signal sensing and analysis. Optical signals may be separately recorded for each microchamber 112, and may be measured simultaneously or at different times, as desired.

Figure 6:
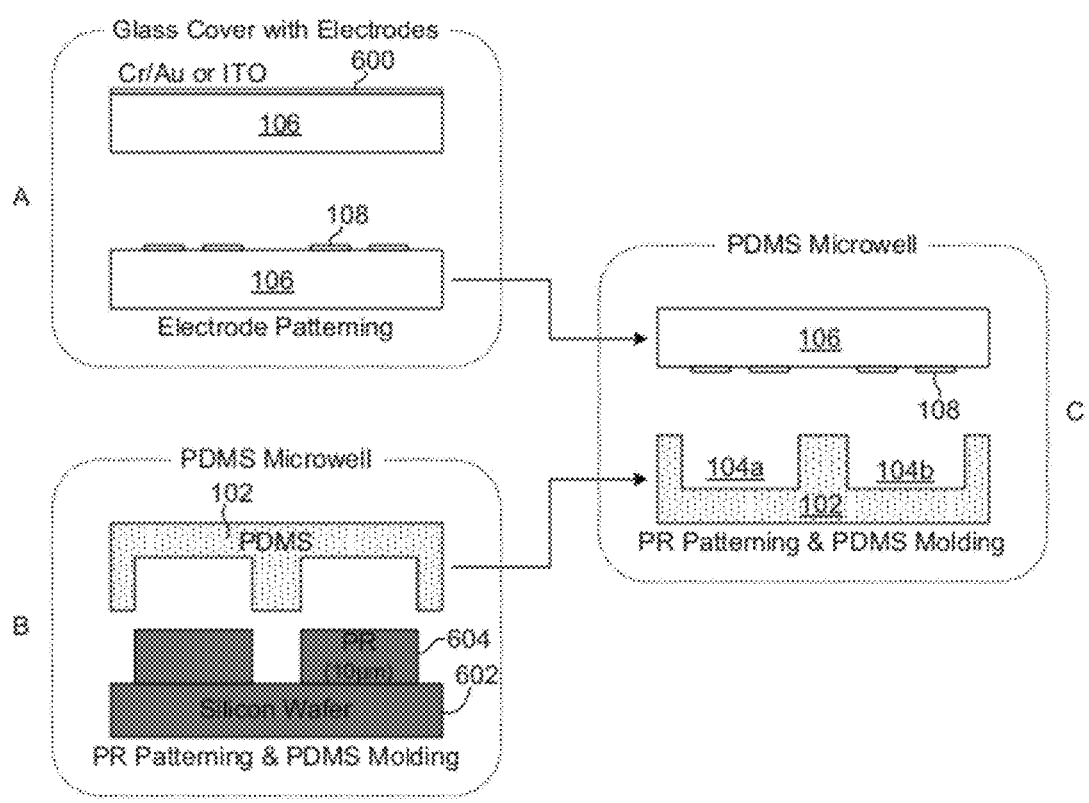
FIG. 6 is a schematic flow diagram of a fabrication process associated with an apparatus for analyzing individual cell composition in accordance with embodiments of the invention.

One embodiment of a fabrication process for an apparatus 100 in accordance with the present invention is illustrated in FIG. 6. As previously mentioned, the apparatus 100 may be fabricated from commonly-used micro-fabrication materials that are compatible with cells 120 and cell buffer solutions 126, such as glass, gold or indium tin oxide ("ITO") electrodes, and polydimethylsiloxane ("PDMS").

In any event, either or both of the deposition plate 102 and the cover plate 106 may be fabricated from a substantially flexible material to facilitate isolation of single cells in each microwell 104. Further, at least one of the deposition plate 102 and the cover plate 106 may be substantially transparent to facilitate optical measurements and analysis. Two separated, opposite electrodes 108 may correspond to each microwell 104 to enable electrical cell lysis in the isolated microchambers 112. Electrode 108 dimensions may determine conditions of electrical cell lysis in the microchambers 112.

As shown in FIG. 6, in some embodiments, a Cr/Au or ITO layer 600 may be deposited on a glass wafer 600 to produce a glass cover plate 106 with electrodes 108 properly positioned to enable cell lysis within each microchamber 112. The electrodes 108 may be geometrically patterned on the wafer 600 using known micro-fabrication and patterning techniques. In this manner, two separated, opposite electrodes 108 may correspond to each microwell 104 in the deposition plate 102. The two opposite electrodes 108 may apply an electric field to the corresponding microchamber 112 (upon application of the cover plate 106) to lyse one or more cells 120 therein.

In one embodiment, for example, the electric field may attract one or more cells 120 to the electrodes 108 with positive dielectrophoresis, and may lyse the cells 120 with electroporation. This two-step process may reduce the critical voltage for cell lysis, thus preventing unwanted electrolysis of the buffer 126. The presence of electrodes 108 corresponding to each microchamber 112 may also allow electrochemical analysis of cytoplasmic components following electrical lysis.

In one embodiment, an array of one hundred rows and one hundred columns (10,000 microwells 104), may include one hundred electrodes 108 connected in parallel. In other embodiments, electrical connections may be provided to each individual microchamber 112 using technology developed in CCD design, for example. In CCD technology, each individual pixel delivers an electrical signal depending on the photons collected. Similarly, in embodiments of the present invention, each microchamber 112 may generate an electrical signal depending on the electrochemical composition of each chamber. Signals may also be fed to each individual microchamber 112 to manipulate or lyse the cells. In other embodiments, electrochemical analysis may include a variety of options known to those in the art, such as nanowire detection.

The deposition plate 102 and microwells 104 may be fabricated according to known micro-molding techniques. In one embodiment, for example, a silicon wafer 602 may include a 10.0 μm negative photoresist layer 604 patterned to form appropriately-sized microwells 104 in a deposition plate 102 made of PDMS. Specific microwell 104 dimensions may be selected depending on characteristics and dimensions of the cells to be analyzed, as discussed in more detail with reference to FIGS. 8 and 9, below.

As shown, the cover plate 106 may overlie the deposition plate 102 and may be positioned such that two separate, opposite electrodes 108 correspond to each microwell 104. In certain embodiments, precise alignment between the deposition plate 102 and the cover plate 106 may not be required as the microwells 104 and electrodes 108 may be sized and patterned such that at least two opposite electrodes may correspond to any one microchamber 112 at any position.

Some alternative embodiments of an apparatus 100 in accordance with the invention are illustrated in FIGS. 7a-7d. As shown, fabrication materials and characteristics may be selected such that certain portions of the apparatus 100 or deposition plate 102 may be substantially opaque. Such design choices may be motivated by the type of optical analysis to be performed. Indeed, in some embodiments, substantially opaque sidewalls 700 or microwells 104 may reduce interference between optical signals produced in adjacent or neighboring microchambers 112, making it easier to distinguish the source of chemical reactions.

In any case, either or both of the deposition plate 102 and the cover plate 106 may be fabricated from a substantially flexible material to facilitate isolation of single cells in each microwell 104, and either or both of the deposition plate 102 and the cover plate 106 may be substantially transparent to facilitate optical measurements and analysis.

Figure 7A:
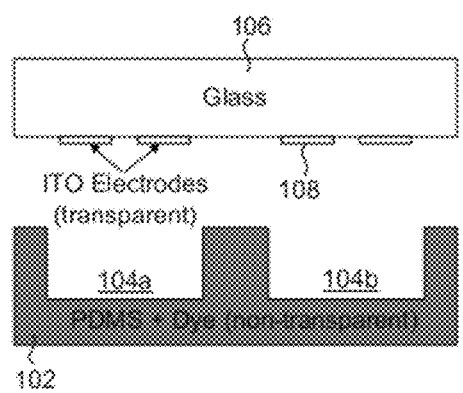
FIGS. 7a-7d illustrate various embodiments of a deposition plate and cover in accordance with the invention.
Figure 7B:
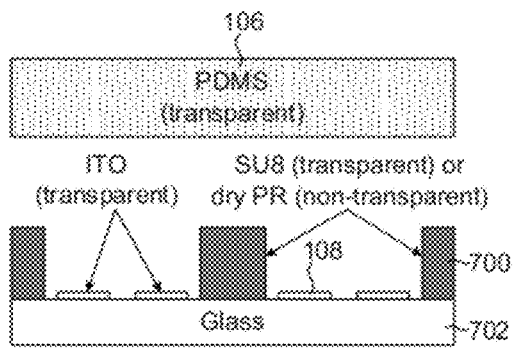
Figure 7C:
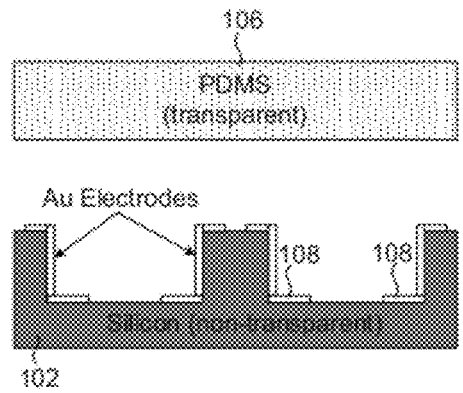

As shown in FIGS. 7a and 7c, certain embodiments of a deposition plate 102 may be fabricated from a substrate (such as PDMS or silicon) that includes a dye to render the deposition plate 102 substantially opaque. The cover plate 106 and/or the electrodes 108 may be substantially transparent.

For example, as shown in FIG. 7a, the cover plate 106 may be glass, and may have substantially transparent ITO electrodes 108 patterned thereon. In other embodiments, as shown in FIG. 7c, the cover plate 106 may be formed from substantially transparent PDMS. The electrodes 108, on the other hand, may be gold and substantially opaque. Thus, in this embodiment, the electrodes 108 may be positioned adjacent the deposition plate 102 so as not to impede microchamber 112 visibility. In both embodiments, the transparency of the cover plate 106 may enable optical analysis, while the flexibility of the deposition plate 102 (in FIG. 7a) and the cover plate 106 (in FIG. 7c) may facilitate single cell isolation.

Figure 7D:
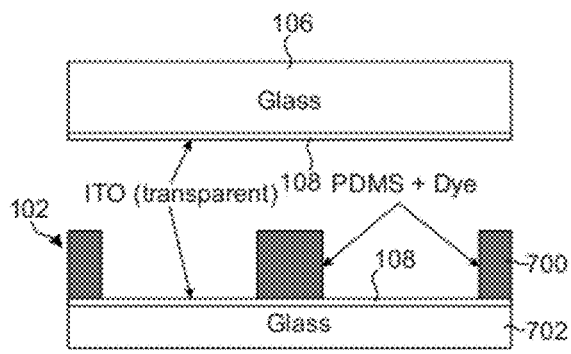

In other embodiments, as shown in FIGS. 7b and 7d, the deposition plate 102 may include substantially opaque sidewalls 700 and a substantially transparent base plate 702. The cover plate 106 may also be substantially transparent. In this manner, optical analysis may be performed through either or both of the deposition plate 102 and cover plate 106, while the opacity of the sidewalls 700 may prevent unwanted interference between optical signals produced in neighboring microchambers 112.

In one embodiment, as shown in FIG. 7b, the cover plate 106 may be formed of substantially transparent PDMS. The deposition plate 102 may include a glass base plate 702 and substantially transparent or opaque sidewalls 700, depending on the sidewall 700 material used. In certain embodiments, for example, the sidewalls 700 may be made of a substantially transparent photoresist, such as SU-8. In other embodiments, the sidewalls 700 may be made of a substantially opaque photoresist, such as dry film photoresist. Substantially transparent electrodes 108 made of ITO, for example, may be deposited onto the glass base plate 702 so as not to interfere with optical analysis processes.

In another embodiment, as shown in FIG. 7d, both the cover plate 106 and the base plate 702 may be glass. Substantially transparent electrodes 108 formed of ITO, for example, may be deposited onto each of the cover plate 106 and base plate 702. Substantially opaque sidewalls 700 formed of PDMS and dye, for example, may separate and distinguish adjacent microwells 104 of the deposition plate 102.

Figure 8:
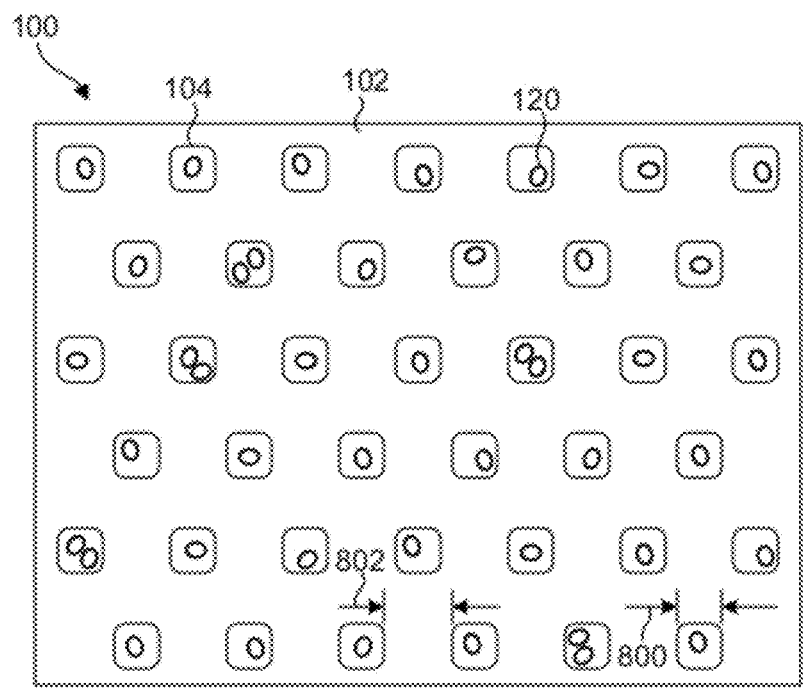
FIG. 8 is a top view of single cells collected in microwells of a deposition plate in accordance with embodiments of the invention.

Referring now to FIG. 8, single-cell collection and overall apparatus 100 performance may depend on microwell 104 dimensions, microwell 104 pitches 802, and electrode dimensions. Microwell 104 diameter 800 and depth may affect cell occupancy in the cellular loading process, as discussed in more detail with reference to FIG. 9 below, while microwell 104 pitch 802 may affect fluidic and optical isolation between isolated microchambers 112. Of course, one skilled in the art will recognize that microwell 104 dimensions, microwell 104 pitches, and electrode dimensions may be selected and varied according to the dimensions and properties of cells 120 to be tested.

In some embodiments, microwell 104 dimensions, microwell 104 pitches, and electrode dimensions may vary within a single apparatus 104. For example, each microwell 104 in certain rows or columns may have a same diameter (8 μm, for example), while each microwell 104 in other rows or columns may have a different diameter (12 μm, for example). Such a design may facilitate single-cell loading in a heterogeneous cell population where cells 120 vary in size, or may serve other purposes known to those in the art.

In one embodiment, apparatus 100 design may include a microwell 104 diameter 800 of 12 μm, a microwell 104 depth of 10 μm, a microwell 104 pitch 802 of 12 μm, an electrode width of 3 μm, and an electrode pitch of 3 μm. Advantageously, this design may produce a final apparatus 100 having ten thousand chambers 112, a small surface area (1.9 mm by 2.6 mm), and may not require alignment between the microwells 104 and the electrodes 108, since at least two opposite electrodes 108 may be associated with one microchamber 112 at any position.

Figure 9:
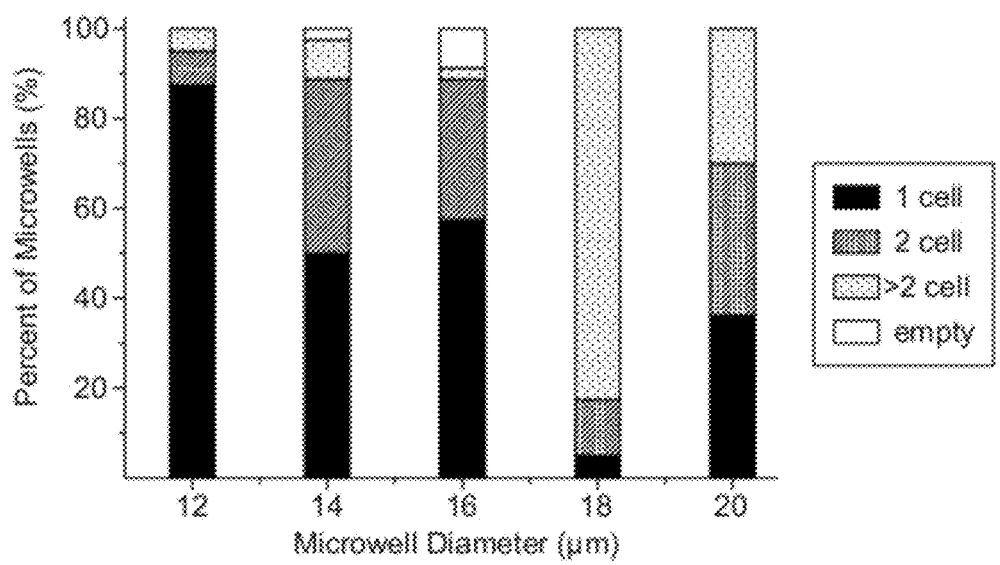
FIG. 9 is a graph of an exemplary distribution of microwell cell occupancies for a range of microwell diameters in accordance with certain embodiments.

In certain embodiments, microwell 104 diameter 800 in particular may have a significant impact on a distribution of microwell 104 occupancies for cells 120 of a particular size. As shown in FIG. 9, in one experiment, red blood cells 120 having an average diameter of 8 μm were tested for single-cell distribution in microwells 104 having varying diameters 800. Of each microwell 104 diameter tested, microwells 104 measuring 12 μm in diameter 800 achieved the highest rate of success for single-cell loading. Indeed, 87.2% of microwells 104 were occupied with single cells 120 when loaded in accordance with embodiments of the invention. Single-cell loading was much less successful in microwells 104 having increased diameters 800, as shown.

Figure 10A:
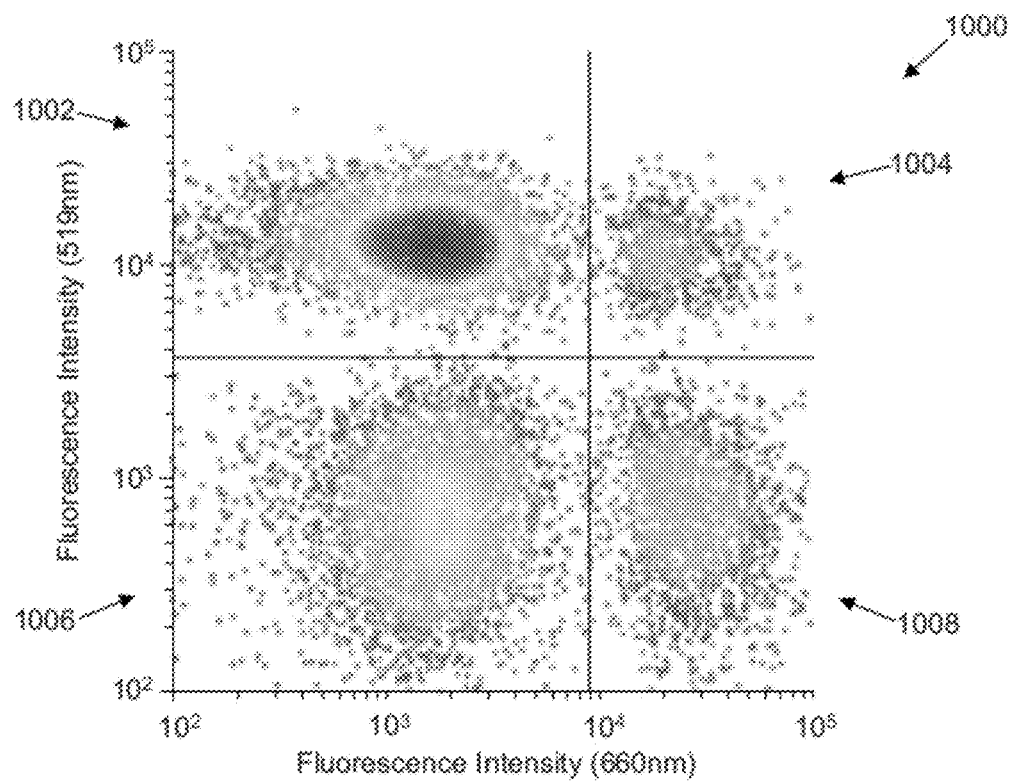
FIG. 10a is a two-dimensional dot plot representing observed fluorescence associated with each microchamber in accordance with one embodiment of the invention.
Figure 10B:
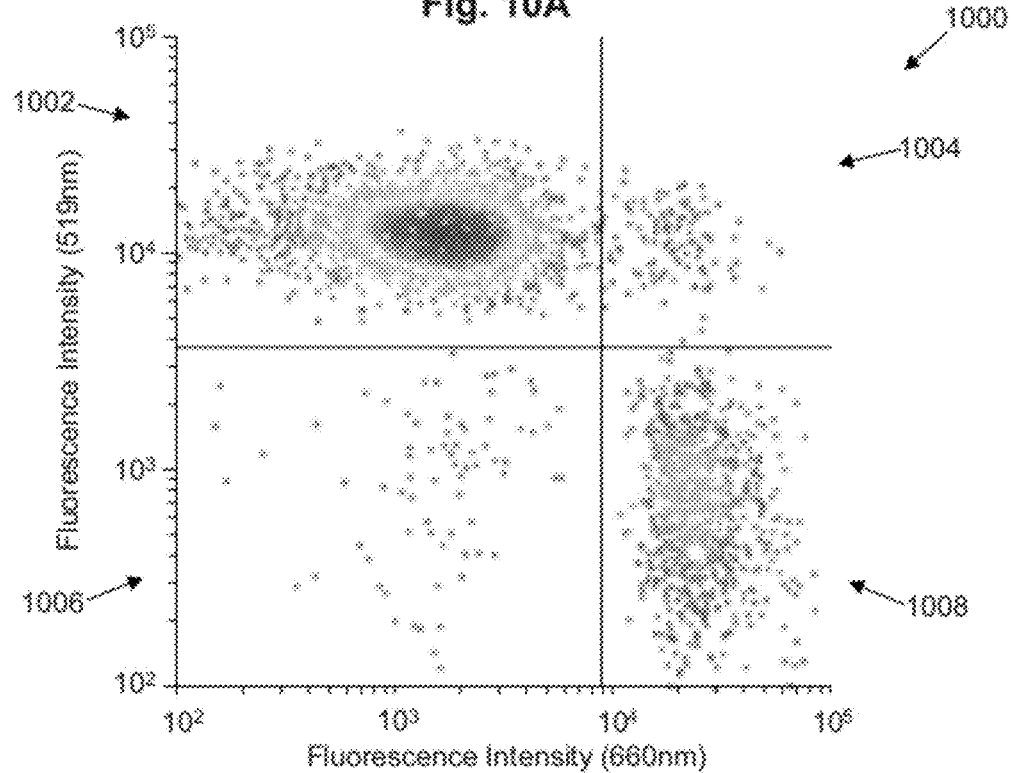
FIG. 10b is the dot plot of FIG. 10b excluding "no-cell" and "multiple cell" events.

Referring now to FIGS. 10a-10c, the present inventors conducted an experiment to verify their overall approach in loading and analyzing cells 120 in accordance with embodiments of the invention. This experiment analyzed a heterogeneous mixture of cells sub-optimally loaded into an array of eighty-eight by one hundred sixteen microwells 104 (10,208 total), resulting in a significant number of microchambers 112 with either no or multiple cells.

The array of microwells 104 was fabricated with a glass cover plate 106 and gold electrodes 108. Allophycocyanin ("APC") was used to label glycophorin A on the surface of one portion of a red blood cell population. These APC-labeled cells were mixed with cells loaded in the cytosol with Fluo-4 ("Invitrogen"), a fluorescently green calcium indicator. The mixture of APC- and Fluo-4 cells was loaded into the microwells 104 in a calcium-containing buffer 126.

The fluorescence of Fluo-4 is strongly dependent on calcium concentration. Accordingly, the low calcium concentration inside normal red blood cells may result in low green fluorescence in microchambers 112 containing intact Fluo-4 cells. Microchambers 112 that contain cells 120 that are not able to maintain a low calcium concentration, or that are lysed, may show a strong green fluorescence. After the microchambers 112 have been closed, image analysis in normal light may determine the presence of cells 120 in the chambers 112.

According to one aspect of the experiment, fluorescent analysis was performed prior to application of a voltage pulse across the microchambers 112. This analysis identified chambers 112 that contained APC-labeled cells (red), cells that were lysed before intentional disruption of the membrane (green), and chambers that contained both lysed Fluo-4 cells and APC-cells (yellow). Less than 0.5% of the microchambers 112 indicated unintentional lysis of the cells during the loading and closure procedures.

According to another aspect of the experiment, the array of 10,208 microchambers 112 was analyzed after application of a voltage pulse across the microchambers 112 to disrupt the cell membranes. Microchambers 112 with only APC cells appeared red under fluorescent imaging procedures, chambers 112 with Fluo-4 cells appeared green (as the cytosol with Fluo-4 interacted with extracellular calcium), and chambers 112 with both APC and Fluo-4 cells appeared yellow.

FIG. 10a is a two-dimensional dot plot 600 showing the observed fluorescence of each event (microchamber 112) after application of the voltage pulse, as described above. As shown, dots in the upper-left quadrant 1002 represent the 3,702 microchambers 112 having green fluorescence; dots in the upper-right quadrant 1004 represent the 761 microchambers 112 with yellow fluorescence; dots in the lower-left quadrant 1006 represent the 3,806 microchambers 112 with low fluorescence; and dots in the lower-right quadrant 1008 represent the 1,939 microchambers 112 with red fluorescence.

Image analysis software was then programmed to exclude no-cell and multiple-cell events. The results of this image analysis are shown in FIG. 10b. From the lower-left quadrant 1006 (no cell) and upper-right quadrants 604 (both Fluo-4 and APC cells), events were effectively removed. Of the 4,567 events in these chambers 112, only 187 (about 4%) were not removed by image recognition, and manual analysis of these events showed that the majority were empty chambers 112 or chambers 112 with multiple cells recognized incorrectly due to unwanted shadows of electrodes 108 or other defects. Similarly, multiple-cell events were effectively removed from the upper-left 1002 and lower-right 1008 quadrants, leaving 2,133 and 864 events, respectively, in these quadrants 1002, 1008.

In this experiment, only 19 single cells (about 0.6%) were not lysed. The combined results of this experiment show that even with suboptimal loading, statistically relevant data may be collected on cell populations using image analysis in accordance with embodiments of the invention. Specifically, this experiment indicates that embodiments of the invention may distinguish individual cells in mixed populations, and may detect cytoplasmic compounds corresponding to such cells accurately and efficiently. Indeed, embodiments of the present invention compare favorably with well-established, albeit less efficient, flowcytometric evaluation of mixed cell populations.

Another advantage of this approach is the ability of embodiments of the invention to monitor single cells over time. Indeed, unlike flow cytometry, embodiments of the present invention may allow measurement of cytoplasmic components that may not be detectable or measurable under fast-response conditions. Particularly, certain embodiments may enable measurement of enzymatic activities based on substrate breakdown.

Figure 11A:
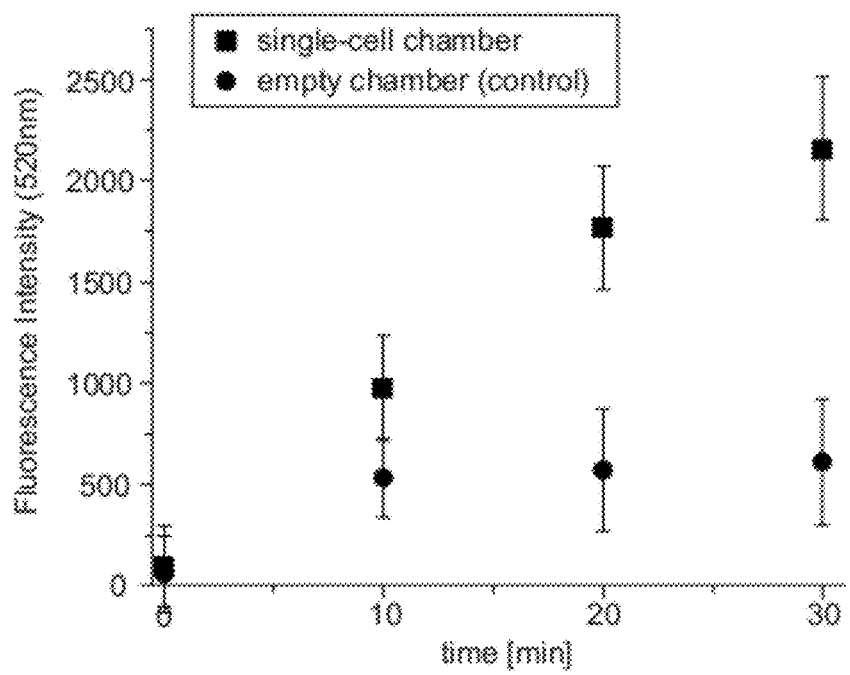
FIG. 11a is a graph comparing fluorescence intensities of microchambers with no cells and single cells after cell lysing in accordance with one embodiment of the invention.
Figure 11B:
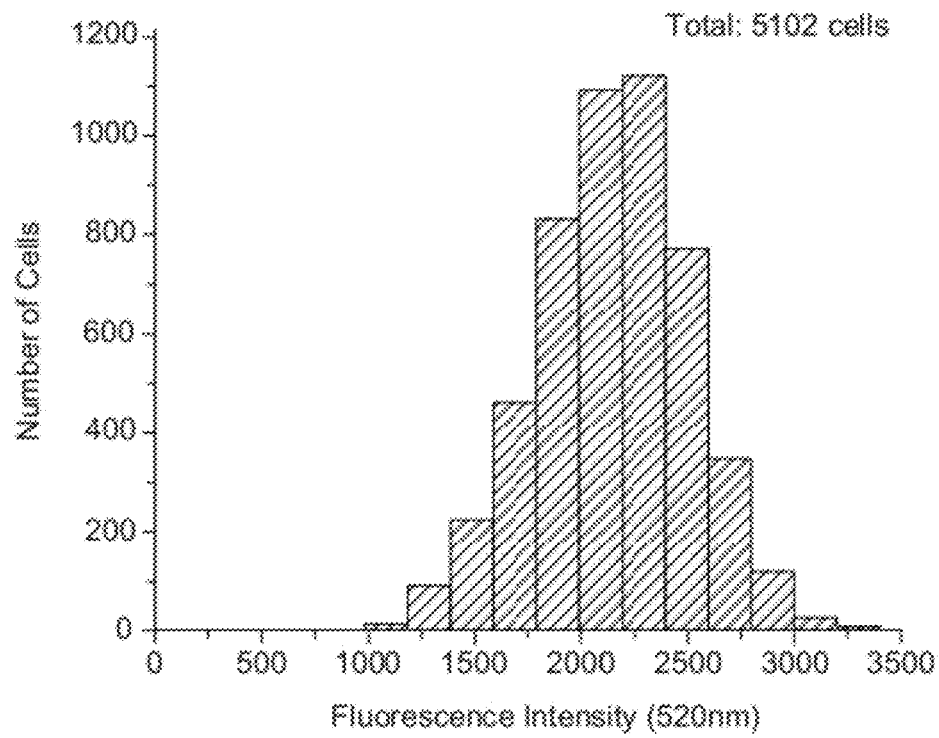
FIG. 11b is a graph comparing fluorescence intensities from the single cells of FIG. 11a after thirty minutes.

As shown in FIGS. 11a and 11b, for example, the present inventors conducted an experiment to measure caspase-3 activity with the fluorogenic substrate Z-DEVD-R110 (Molecular Probes), in accordance with embodiments of the present invention.

Red blood cells 120 in which caspase-3 was activated were loaded into microwells 104 in a buffer 126 containing Z-DEVD-R110. A cover plate 106 was then affixed to form isolated microchambers 112 corresponding to each microwell 104, and electrodes 108 were actuated to lyse the cells 120 therein.

FIG. 11a compares fluorescence intensities of microchambers 112 with no cells and single cells after electrical disruption of the red cell membranes. Immediately after cell lysis, both empty chambers 112 and chambers 112 with a single cell exhibited low fluorescence (61±190 and 80±200 AU, respectively). Fluorescence in empty microchambers 112 increased slightly over time, indicating a low level of substrate breakdown in the buffer 126. In contrast, microchambers 112 with single cells 120 generated a substantial increase in fluorescence over time, as the breakdown of the substrate by caspase-3 released from the cytosol progressed.

As those skilled in the art will recognize, fluorescence increase in a microchamber 112 over time may indicate enzyme activity of single cells 120 in cell populations. Under the conditions of this experiment, fluorescence increase was still in the linear phase at thirty (30) minutes in virtually all microchambers 112. A graph of caspase-3-induced fluorescence from single cells 120 after thirty (30) minutes is shown in FIG. 11b, and represents the distribution of the relative activity of caspase-3 in single cells 120 in large cell populations (5,102 cells).

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus for analyzing individual cell composition in a heterogeneous cell population, the apparatus comprising:
   a deposition plate having an array of microwells disposed therein;
   a cover plate overlying the deposition plate and sealing the microwells of the array of microwells from one another and sealing the microwells of the array of microwells, the cover plate having a planar lower surface, each microwell of the array of microwells and a portion of the planar lower surface over the each microwell defining a sealed volume; and
   a pair of electrodes associated with at least one microwell in the deposition plate and configured to generate an electric field within the at least one microwell, the pair of electrodes being formed on the portion of the planar lower surface over the at least one microwell.

2. The apparatus of claim 1, further comprising a power supply connected to the pair of electrodes to apply an electrical potential thereacross.

3. The apparatus of claim 1, wherein the pair of electrodes is coupled to the cover plate.

4. The apparatus of claim 1, wherein each microwell comprises dimensions selected to accommodate a single cell.

5. The apparatus of claim 4, wherein the cover plate forms a closed chamber corresponding to each microwell.

6. The apparatus of claim 1, wherein at least one of the deposition plate and the cover plate is substantially transparent.

7. The apparatus of claim 6, wherein at least one of the deposition plate and the cover plate comprises glass.

8. The apparatus of claim 1, wherein the pair of electrodes comprises one of gold and indium tin oxide.

9. The apparatus of claim 1, wherein at least one of the deposition plate and the cover plate is substantially flexible.

10. The apparatus of claim 1, wherein at least one of the deposition plate and the cover plate comprises polymethylsiloxane ("PDMS").

11. The apparatus of claim 1, wherein each microwell comprises at least one substantially opaque sidewall, the at least one substantially opaque sidewall extends perpendicular to the cover plate.

12. A method for analyzing individual cell composition in a heterogeneous cell population, the method comprising:
depositing, onto a deposition plate having an array of microwells disposed therein, a cell suspension comprising a heterogeneous cell population;
covering the deposition plate with a cover plate, the cover plate isolating a single cell in at least one microwell, the cover plate effective to seal the microwells of the array of microwells with respect to one another, the cover plate further comprising an array of electrode pairs, each electrode pair of the array of electrode pairs positioned over an opening of one microwell of the array of microwells, the cover plate having a planar lower surface, each microwell of the array of microwells and a portion of the planar lower surface over the each microwell defining a sealed volume; and
generating an electric field within the at least one microwell to lyse the single cell by applying an electric potential across the electrodes of the electrode pair of the array of electrode pairs sufficient to lyse the single cell.

13. The method of claim 12, wherein covering the deposition plate further comprises forming closed chambers corresponding to each microwell.

14. The method of claim 12, further comprising applying a buffer to the surface of the deposition plate to remove excess cells from the microwells.

15. The method of claim 12, wherein the cell suspension further comprises a buffer including at least one detection agent.

16. The method of claim 12, further comprising performing a cell count to verify isolation of the single cell in the at least one microwell.

17. The method of claim 16, wherein performing the cell count comprises utilizing microscopy scanning.

18. The method of claim 16, wherein performing the cell count comprises utilizing a charge-coupled device ("CCD") to determine a number of cells in the at least one microwell.

19. The method of claim 12, further comprising monitoring at least one microwell for a chemical reaction between the at least one detection agent and cytoplasm from the single cell.

20. The method of claim 19, wherein the at least one chemical reaction produces an optical response.

21. The method of claim 20, wherein the optical response comprises at least one of fluorescence, chemiluminescence, and absorbance.

22. The method of claim 12, wherein generating the electrical field comprises positioning a pair of electrodes within each microwell.

23. The method of claim 22, wherein generating the electrical field further comprises applying a voltage pulse across the pair of electrodes.

* * * * *